United States Patent
Hyung et al.

(10) Patent No.: US 11,666,248 B2
(45) Date of Patent: Jun. 6, 2023

(54) INFORMATION PROCESSING APPARATUS AND OPERATING METHOD THEREOF

(71) Applicant: Samsung Electronics Co., Ltd., Suwon-si (KR)

(72) Inventors: Seungyong Hyung, Yongin-si (KR); Jun-Won Jang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 648 days.

(21) Appl. No.: 16/654,456

(22) Filed: Oct. 16, 2019

(65) Prior Publication Data

US 2020/0237260 A1 Jul. 30, 2020

(30) Foreign Application Priority Data

Jan. 30, 2019 (KR) .................. 10-2019-0012110

(51) Int. Cl.
*A61B 5/11* (2006.01)
*A61H 3/00* (2006.01)

(52) U.S. Cl.
CPC ................ *A61B 5/112* (2013.01); *A61H 3/00* (2013.01); *A61B 2562/0219* (2013.01); *A61H 2003/007* (2013.01); *A61H 2201/165* (2013.01); *A61H 2201/5069* (2013.01); *A61H 2201/5079* (2013.01); *A61H 2201/5084* (2013.01)

(58) Field of Classification Search
None
See application file for complete search history.

(56) References Cited

U.S. PATENT DOCUMENTS

| | | | |
|---|---|---|---|
| 9,974,478 B1* | 5/2018 | Brokaw | A61B 5/486 |
| 2005/0177080 A1* | 8/2005 | Yasuhara | A61H 1/0244 |
| | | | 602/16 |
| 2012/0215140 A1* | 8/2012 | Hirata | A61H 3/00 |
| | | | 601/35 |
| 2016/0074272 A1* | 3/2016 | Ahn | A61B 5/1122 |
| | | | 623/24 |
| 2016/0106616 A1* | 4/2016 | Kim | A61B 5/7264 |
| | | | 702/145 |

(Continued)

FOREIGN PATENT DOCUMENTS

| | | |
|---|---|---|
| JP | 6295337 B2 | 3/2018 |
| JP | 2018082755 A | 5/2018 |

(Continued)

OTHER PUBLICATIONS

Patterson, Kara K., et al. "Evaluation of gait symmetry after stroke: a comparison of current methods and recommendations for standardization." Gait & posture 31.2 (2010): 241-246. (Year: 2010).*

(Continued)

*Primary Examiner* — Benjamin S Melhus
(74) *Attorney, Agent, or Firm* — Harness, Dickey & Pierce, P.L.C.

(57) ABSTRACT

A method of operating an information processing apparatus may include collecting gait information of a walking assistance apparatus; determining a gait feature of a user of the walking assistance apparatus based on the collected gait information; and controlling the walking assistance apparatus by determining a gait group of the user based on the determined gait feature.

16 Claims, 10 Drawing Sheets

(56) References Cited

U.S. PATENT DOCUMENTS

| | | | |
|---|---|---|---|
| 2016/0184985 A1* | 6/2016 | Shim | B25J 9/1671 |
| | | | 623/32 |
| 2016/0192863 A1* | 7/2016 | Zhong | A61B 5/112 |
| | | | 600/595 |
| 2017/0020765 A1* | 1/2017 | Lim | A61H 1/0244 |
| 2018/0092536 A1 | 4/2018 | Sandler et al. | |
| 2018/0178065 A1* | 6/2018 | Yu | A63B 24/0075 |
| 2018/0214768 A1 | 8/2018 | Macri et al. | |
| 2018/0221237 A1 | 8/2018 | Swift et al. | |
| 2020/0039061 A1* | 2/2020 | Sankai | A61H 1/024 |

FOREIGN PATENT DOCUMENTS

| | | |
|---|---|---|
| KR | 20120071555 A | 7/2012 |
| KR | 101454291 B1 | 10/2014 |
| KR | 20150066185 A | 6/2015 |
| KR | 20160031246 A | 3/2016 |
| WO | WO-2015047499 A2 | 4/2015 |
| WO | WO-2017186591 A1 | 11/2017 |

OTHER PUBLICATIONS

Filli, Linard et al. "Profiling walking dysfunction in multiple sclerosis: characterisation, classification and progression overtime." Scientific reports vol. 8,1 4984. Mar. 21, 2018, doi:10.1038/s41598-018-22676-0 (Year: 2018).*

* cited by examiner

INFORMATION PROCESSING APPARATUS AND OPERATING METHOD THEREOF

CROSS-REFERENCE TO RELATED APPLICATION

This application claims priority under 35 U.S.C. § 119 to Korean Patent Application No. 10-2019-0012110, filed on Jan. 30, 2019, in the Korean Intellectual Property Office, the entire contents of which are incorporated herein by reference in their entirety.

BACKGROUND

1. Field

Some example embodiments relate to controlling a walking assistance apparatus.

2. Description of the Related Art

With the current onset of the aging society, an increasingly large number of people suffer from pain and discomfort due to joint issues. The developments in the medical field have also brought the life extension. However, as the quality of life is emphasized through the healthy life, a concept of service that assists the elderly or disabled people to live like people who do not suffer from such pain and discomfort is emphasized. In particular, there is an increasing interest in a walking assistance apparatus that may assist elderly people or patients having walking issues due to their uncomfortable joints.

SUMMARY

Some example embodiments relate to a method of operating an information processing apparatus.

In some example embodiments, the method may include collecting gait information associated with a walking assistance apparatus; determining a gait feature of a user of the walking assistance apparatus based on the gait information; and controlling the walking assistance apparatus based on the gait feature.

In some example embodiments, the determining the gait feature includes determining gait indices of the user based on the gait information; and generating a gait feature vector based on the gait indices.

In some example embodiments, the gait indices include at least one of a walking speed of the user, a number of steps of the user, a step length of the user, a gait symmetry of the user, a motion range of the user in a roll direction of walking, and a motion range of the user in a pitch direction of walking.

In some example embodiments, the gait symmetry indicates a level of symmetry between legs of the user while the user is walking.

In some example embodiments, the controlling includes determining a gait group of the user based on a gait feature vector corresponding to the gait feature that is within a range that includes a walking speed of the user; and transmitting walking strategy information associated with the gait group.

In some example embodiments, the controlling further includes applying a weight vector to the gait feature vector.

In some example embodiments, the determining the gait feature includes determining a walking speed of the user based on at least one of acceleration information and angular velocity information associated with the walking assistance apparatus; and determining a gait symmetry of the user based on a first ratio and a second ratio, the first ratio being a time of a swing phase over a time of a stance phase of a left foot of the user, and the second ratio being a time of a swing phase over a time of a stance phase of a right foot of the user.

In some example embodiments, the determining the gait feature includes determining a number of steps of the user based on a swing count of an encoder associated with the walking assistance apparatus; and determining a step length of the user based on at least one of a motion range, an angular velocity range, and an angular acceleration range of hip joints of the user.

In some example embodiments, the determining the gait feature includes determining an angle of a motion in each of a roll direction and a pitch direction based on measurements obtained by an inertial sensor associated with the walking assistance apparatus.

In some example embodiments, the gait information includes at least one of (i) acceleration information and angular velocity information associated with the walking assistance apparatus and (ii) angle information and angular velocity information associated with the walking assistance apparatus.

Some example embodiments relate to an information processing apparatus.

In some example embodiments, the information processing apparatus includes a memory configured to store gait information associated with a walking assistance apparatus; and a processor configured to, determine a gait feature of a user of the walking assistance apparatus based on the gait information, and control the walking assistance apparatus based on the gait feature.

In some example embodiments, the processor is further configured to, determine gait indices of the user based on the gait information, and generate a gait feature vector based on the gait indices.

In some example embodiments, the gait indices include at least one of a walking speed of the user, a number of steps of the user, a step length of the user, a gait symmetry of the user, and a motion range of the user in a roll direction of walking, and a motion range of the user in a pitch direction of walking.

In some example embodiments, the gait symmetry indicates a level of symmetry between legs of the user while the user is walking.

In some example embodiments, the processor is further configured to, determine a gait group of the user based on a gait feature vector corresponding to the gait feature that is within a range that includes a walking speed of the user, and transmit walking strategy information associated with the gait group.

In some example embodiments, the processor is further configured to apply a weight vector to the gait feature vector.

In some example embodiments, the processor is further configured to, determine a walking speed of the user based on at least one of acceleration information and angular velocity information of the walking assistance apparatus, and determine a gait symmetry of the user based on a first ratio and a second ratio, the first ratio being a time of a swing phase over a time of a stance phase of a left foot of the user and the second ratio being a time of a swing phase over a time of a stance phase of a right foot of the user.

In some example embodiments, the processor is further configured to, determine a number of steps of the user based on a swing count of an encoder associated with the walking assistance apparatus, and determine a step length of the user based on at least one of a motion range, an angular velocity range, and an angular acceleration range of hip joints of the user.

In some example embodiments, the processor is further configured to determine an angle of a motion in each of a roll direction and a pitch direction based on measurements obtained by an inertial sensor associated with the walking assistance apparatus.

In some example embodiments, the gait information includes at least one of (i) acceleration information and angular velocity information associated with the walking assistance apparatus, and (ii) angle information and angular velocity information associated with the walking assistance apparatus.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
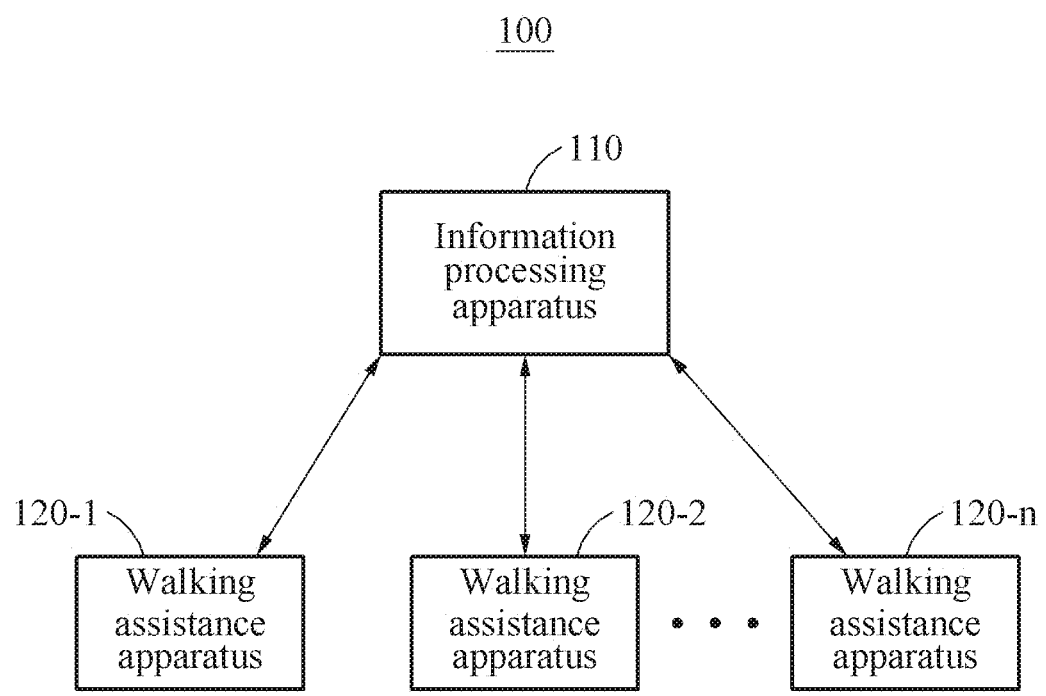
FIG. 1 illustrates an example of a walking system according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit example embodiments to the particular example embodiments disclosed herein. On the contrary, the example embodiments are to cover all modifications, equivalents, and alternatives falling within the scope of the example embodiments. Like numbers refer to like elements throughout the description of the figures.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined herein, all terms used herein including technical or scientific terms have the same meanings as those generally understood by one of ordinary skill in the art. Terms defined in dictionaries generally used should be construed to have meanings matching with contextual meanings in the related art and are not to be construed as an ideal or excessively formal meaning unless otherwise defined herein.

FIG. 1 illustrates an example of a walking system according to at least one example embodiment.

Referring to FIG. 1, a walking system 100 includes an information processing apparatus 110 and a plurality of walking assistance apparatuses 120-1 to 120-$n$.

The information processing apparatus 110 may be configured as a server or a mobile device, for example, a smartphone and a laptop computer.

Each of the walking assistance apparatuses 120-1 to 120-$n$ assists a user with walking. For example, the walking assistance apparatus 120-1 may provide an assistance force to a user based on a torque profile. Likewise, each of the other walking assistance apparatuses 120-2 to 120-$n$ may provide an assistance force to a corresponding user based on a torque profile.

At least one of the walking assistance apparatuses 120-1 to 120-$n$ may be a hip type. A hip-type walking assistance apparatus is described with reference to FIGS. 2 and 3. Also, a portion of the walking assistance apparatuses 120-1 to 120-$n$ may be a type of supporting the entire lower body or a portion of the lower body.

The information processing apparatus 110 collects gait information each of the walking assistance apparatuses 120-1 to 120-$n$. That is, the information processing apparatus 110 receives gait information from each of the walking assistance apparatuses 120-1 to 120-$n$. The gait information may include a measurement result of at least one sensor included in each of the walking assistance apparatuses 120-1 to 120-$n$. The at least one sensor may be, for example, an inertial measurement unit (IMU) sensor, that is, an inertial sensor, and/or an encoder. However, it is provided as an example only.

The information processing apparatus 110 determines a gait feature of a user of each of the walking assistance apparatuses 120-1 to 120-$n$ based on gait information of each of the walking assistance apparatuses 120-1 to 120-$n$. For example, the information processing apparatus 110 may determine gait indices of the user of each of the walking assistance apparatuses 120-1 to 120-$n$ based on the gait information of each of the walking assistance apparatuses 120-1 to 120-$n$ and may generate a gait feature vector of each user based on the determined gait indices. Here, the gait feature vectors may be classified for each walking speed range. In one example embodiment, the gait indices may include at least one of, for example, a walking speed of the user, a number of steps, a step length, a gait symmetry, a motion range in a roll direction in the case of walking, and a motion range in a pitch direction in the cage of walking. A method of determining a gait feature is described below with reference to FIGS. 4 and 5.

The information processing apparatus 110 may control each of the walking assistance apparatuses 120-1 to 120-n by determining a gait group of each user based on the gait feature of the user of each of the walking assistance apparatuses 120-1 to 120-n. For example, the information processing apparatus 110 may perform clustering based on gait feature vectors belonging to each walking speed range. Here, when the user of the walking assistance apparatus 120-1 belongs to a first cluster in the walking speed range of 0 to 1 km/h, the information processing apparatus 110 may transmit walking strategy information, for example, a torque profile or a torque output pattern, of the first cluster to the walking assistance apparatus 120-1. The walking assistance apparatus 120-1 may assist the user with walking based on corresponding walking strategy information in the walking speed range of 0 to 1 km/h, which is described below with reference to FIGS. 6 and 7.

Figure 2:
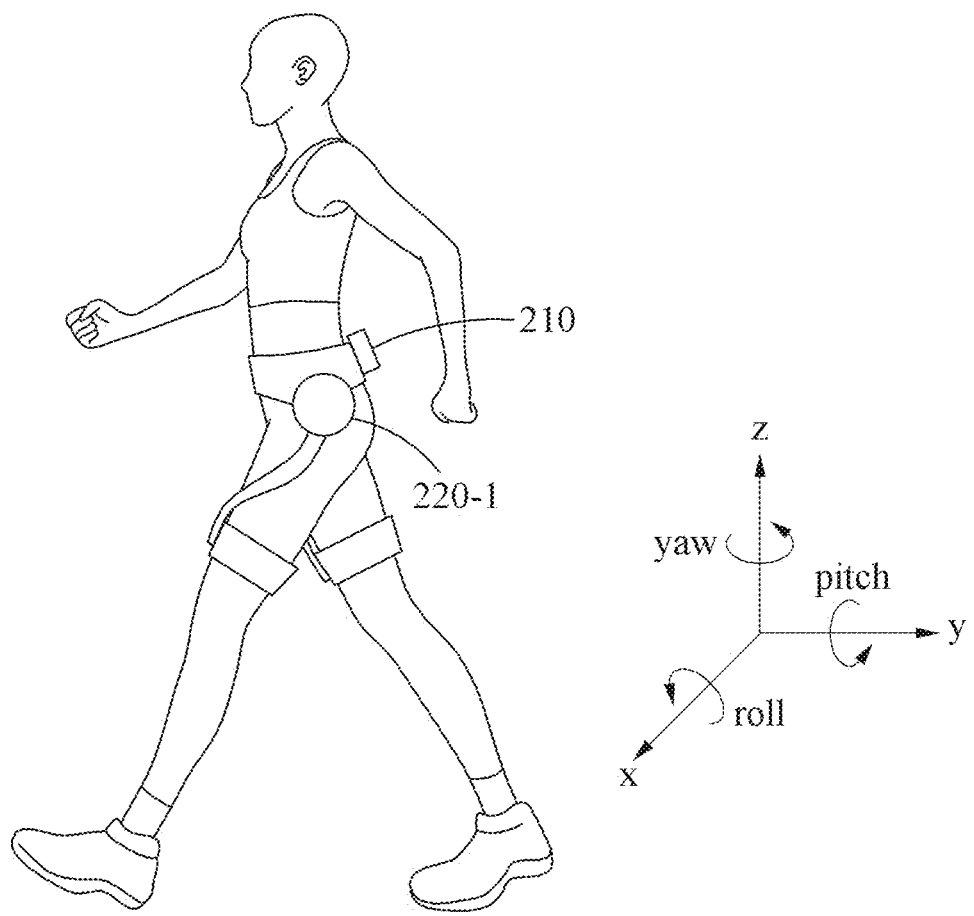
FIGS. 2 and 3 illustrate examples of a walking assistance apparatus according to at least one example embodiment.
Figure 3:
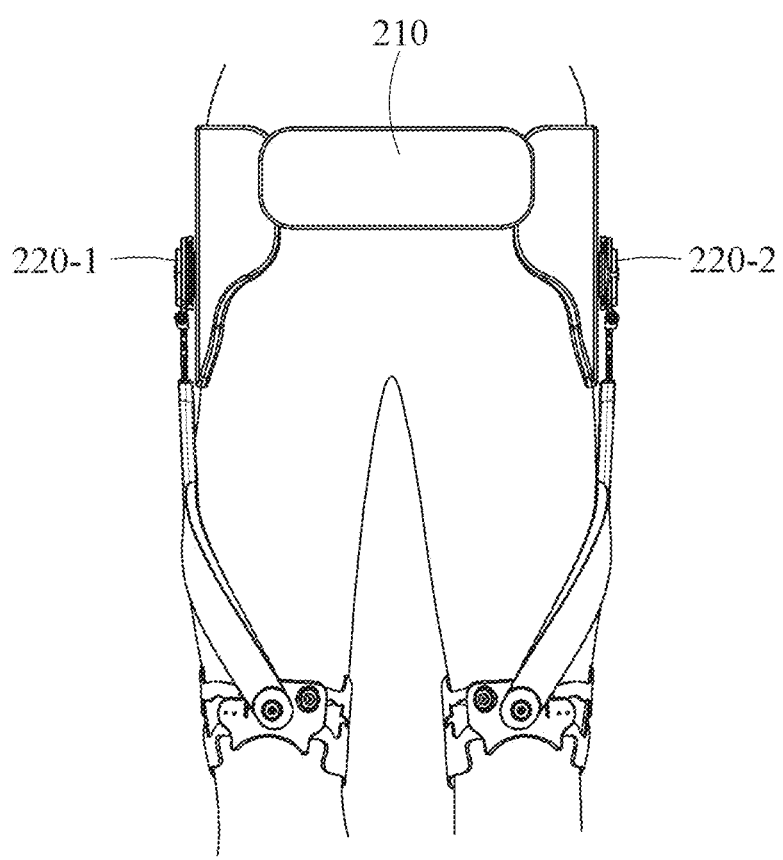

FIGS. 2 and 3 illustrate examples of a walking assistance apparatus according to at least one example embodiment.

Referring to FIGS. 2 and 3, a walking assistance apparatus 120-1 is provided in a hip type. The description of FIGS. 2 and 3 may apply to the walking assistance apparatuses 120-2 to 120-n.

The walking assistance apparatus 120-1 includes an IMU sensor 210, a first encoder 220-1, and a second encoder 220-2.

The IMU sensor 210 may acquire at least one of acceleration information and angular velocity information. For example, the IMU sensor 210 may measure acceleration in each of an x-axial direction, an y-axial direction, and a z-axial direction, in response to walking of the user, and may measure a roll rate, a pitch rate, and a yaw rate.

Although not illustrated in FIGS. 2 and 3, the walking assistance apparatus 120-1 may include a communication interface. For example, the communication interface may include a wired or wireless communication device capable of transmitting and/or receiving information over, for example, a network, in a wired or wireless environment. The walking assistance apparatus 120-1 may transmit at least one of acceleration information and angular velocity information acquired by the IMU sensor 210 to the information processing apparatus 110 through the corresponding communication interface.

The first encoder 220-1 may measure at least one of an angle of a left hip joint and an angular velocity of the left hip joint of the user while the user is walking. The second encoder 220-2 may measure at least one of an angle of a right hip joint and an angular velocity of the right hip joint of the user while the user is walking. The walking assistance apparatus 120-1 may transmit a measurement result of each of the first encoder 220-1 and the second encoder 220-2 to the information processing apparatus 110 through the communication interface.

Figure 4:
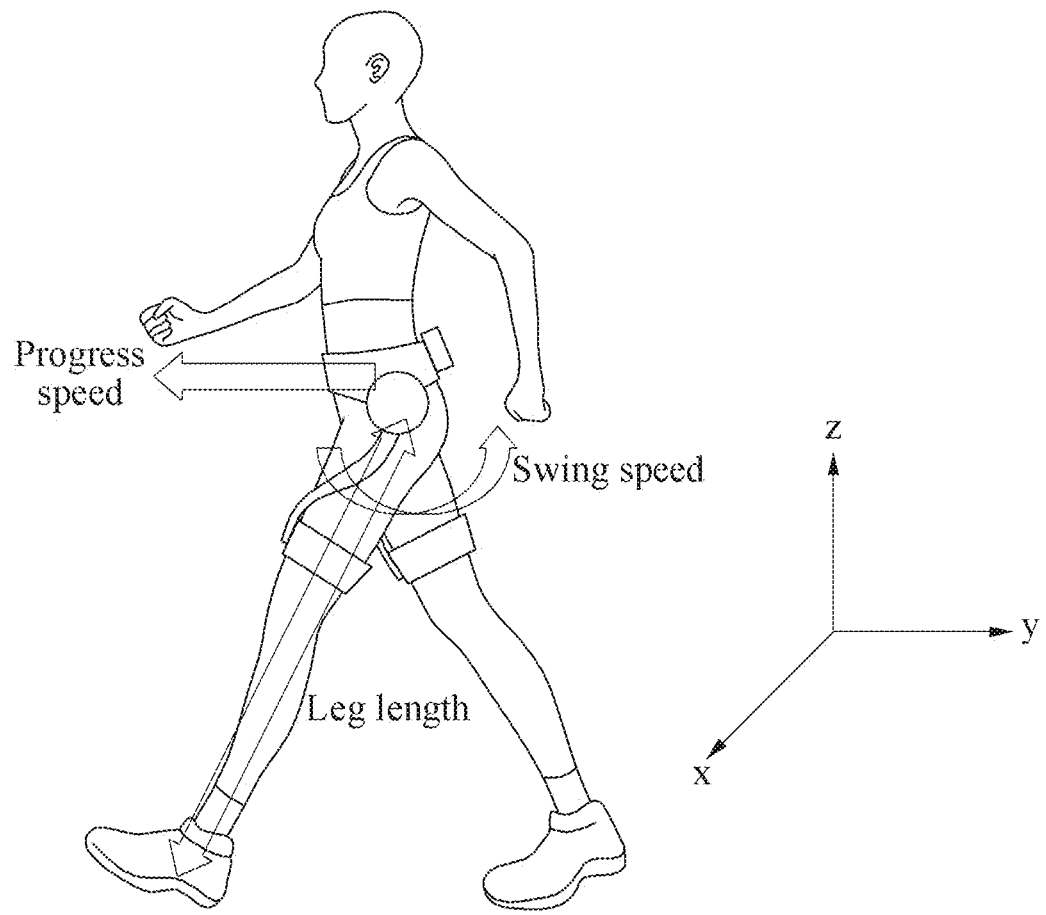
FIGS. 4 and 5 illustrate examples of determining, by an information processing apparatus, a gait feature according to at least one example embodiment.
Figure 5:
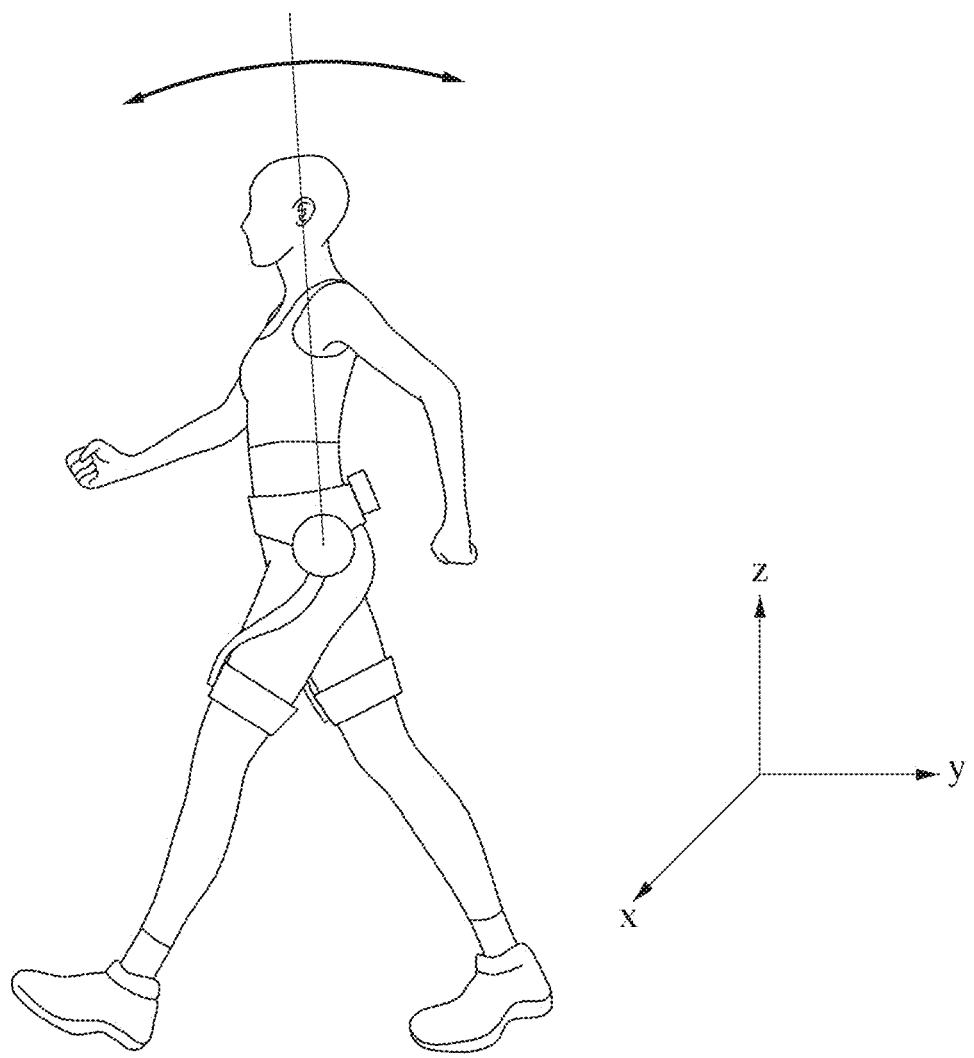

FIGS. 4 and 5 illustrate examples of determining, by an information processing apparatus, a gait feature according to at least one example embodiment.

Referring to FIG. 4, the walking assistance apparatus 120-1 assists the user with walking. Here, the walking assistance apparatus 120-1 transmits a measurement result of each of the IMU sensor 210 and the first encoder 220-1 and the second encoder 220-2 to the information processing apparatus 110.

The information processing apparatus 110 may determine gait indices of the user based on the measurement result of each of the IMU sensor 210, the first encoder 220-1, and the second encoder 220-2. The gait indices may include one or a combination of at least two of, for example, a walking speed, a number of steps, a step length, a gait symmetry, a motion range in a roll direction in the case of walking, and a motion range in a pitch direction in the case of walking. Hereinafter, a process of determining, by the walking assistance apparatus 120-1, each of the walking indices is described.

The information processing apparatus 110 may determine the walking speed of the user. In one example embodiment, the information processing apparatus 110 may calculate the walking speed of the user based on at least one of acceleration information acquired by the IMU sensor 210 and angular velocity information acquired by each of the first encoder 220-1 and the second encoder 220-2. For example, the information processing apparatus 110 may calculate the walking speed according to the following Equation 1.

$$v = \frac{R}{2}(relu(\dot{\theta}_l) + relu(\dot{\theta}_r)) \text{ OR } \int a \qquad \text{[Equation 1]}$$

In Equation 1, v denotes the walking speed, R denotes a leg length of the user, $\dot{\theta}_l$ denotes angular velocity information acquired by the first encoder 220-1, $\dot{\theta}_r$ denotes angular velocity information acquired by the second encoder 220-2, and relu denotes a rectified linear unit (ReLU) function. According to Equation 1, the information processing apparatus 110 may determine the walking speed based on a result value of a ReLU function of the angular velocity information acquired by the first encoder 220-1, a result value of a ReLU function of the angular velocity information acquired by the second encoder 220-2, and the leg length of the user.

In Equation 1, a denotes acceleration information acquired by the IMU sensor 210. According to Equation 1, the information processing apparatus 110 may determine, as the walking speed, an integral value of the acceleration information acquired by the IMU sensor 210.

Depending on example embodiments, the information processing apparatus 110 may determine, as the walking speed of the user, an addition of a result acquired by applying a first weight to $$\frac{R}{2}(relu(\dot{\theta}_l) + relu(\dot{\theta}_r))$$

and a result acquired by applying a second weight to $\int a$.

The information processing apparatus 110 may determine the number of steps of the user. In one example embodiment, the information processing apparatus 110 may calculate a number of steps per unit time (n/t) based on a swing count of the first encoder 220-1 or the second encoder 220-2. For example, when the first encoder 220-1 swings 60 times for 60 seconds, the information processing apparatus 110 may determine that the user has made a single step per second. Depending on example embodiments, the information processing apparatus 110 may calculate the number of steps per unit time by counting a number of impact poles of the walking assistance apparatus 120-1 in a z-axial direction.

The information processing apparatus 110 may determine the step length of the user. In one example embodiment, the information processing apparatus 110 may determine the step length of the user based on at least one of a motion range, an angular velocity range, and an angular acceleration range of both thighs or both hip joints of the user. The motion range of both thighs may include, for example, a maximum angle (L_length_front) and a minimum angle (L_length_rear) of a left hip joint measured by the first encoder 220-1 and a maximum angle (R_length_front) and a minimum angle (R_length_rear) of a right hip joint measured by the second encoder 220-2. The angular velocity range of both thighs may include, for example, a maximum value (R_vel_Max) and a minimum value (R_vel_min) of an angular velocity of a right thigh and a maximum value (L_vel_Max) and a minimum value (L_vel_min) of an angular velocity of a left thigh. The angular acceleration range of both thighs may include, for example, a maximum value (R_acc_Max) and a minimum value (R_acc_min) of angular acceleration of the right thigh and a maximum value (L_acc_Max) and a minimum value (L_acc_min) of angular acceleration of the left thigh.

The information processing apparatus 110 may determine the gait symmetry of the user. The gait symmetry may represent a level of symmetry between both legs of the user while the user is walking. In one example embodiment, the information processing apparatus 110 may determine the gait symmetry of the user based on a ratio between a time of a swing phase and a time of a stance phase of a left foot of the user and a ratio between a time of a swing phase and a time of a stance phase of a right foot of the user. For example, the information processing apparatus 110 may determine the gait symmetry of the user according to the following Equation 2.

$$\text{symmetry} = \log(L\_\text{ratio}/R\_\text{ratio}) \quad \text{[Equation 2]}$$

L_ratio=time of stance phase of left foot/time of swing phase of left foot

R_ratio=time of stance phase of right foot/time of swing phase of right foot

If walking of the user is close to a symmetrical gait, the gait symmetry may be calculated to be close to zero according to Equation 2.

Referring to FIG. 5, the user may perform a motion in a roll direction and a pitch direction while the user is walking. In the case of normal walking, a motion in the roll direction and the pitch direction is barely present. However, if the user rocks during walking, the motion in the roll direction and the pitch direction is present. To represent the motion as a numerical value, the information processing apparatus 110 may calculate at least one of an angle of the motion in the roll direction and an angle of the motion in the pitch direction based on a measurement result of the IMU sensor 210. In one example embodiment, the information processing apparatus 110 may estimate the motion of the user in the roll direction and the motion of the user in the pitch direction by estimating a z-axial gravity component and accordingly, may verify a maximum value (roll_foward) and a minimum value (roll_rear) of roll and may verify a maximum value (pitch_left) and a minimum value (pitch_right) of pitch.

The information processing apparatus 110 generates the gait feature vector based on the determined gait indices. For example, the information processing apparatus 110 may generate the gait feature vector x=[v, n/t, L_length_front, L_length_rear, R_length_front, R_length_rear, symmetry, roll_front, roll_rear, pitch_left, pitch_right].

The information processing apparatus 110 may identify a walking speed range that includes the walking speed v from among the entire walking speed ranges, and may classify the gait feature vector x into the identified walking speed. For example, when the walking speed ranges include 0 to 1 km/h, 1 to 2 km/h, 2 to 3 km/h, and 3 to 4 km/h, and the walking speed is calculated as 0.5 km/h, the information processing apparatus 110 may classify the gait feature vector x into the walking speed range of 0 to 1 km/h.

During an update period T, the information processing apparatus 110 may receive a variety of gait information from the walking assistance apparatus 120-1, may generate a gait feature vector of each piece of gait information, and may classify each gait feature vector into a corresponding walking speed range. An example of a gait feature vector for each walking speed range during the update period T is shown in the following Table 1.

TABLE 1

| 0 to 1 km/h | 1 to 2 km/h | 2 to 3 km/h | 3 to 4 km/h |
|---|---|---|---|
| $x_{\_k}$ | $x_{\_m}$ | $x_{\_n}$ | $x_{\_p}$ |
| $x_{\_k+1}$ | $x_{\_m+1}$ | $x_{\_n+1}$ | $x_{\_p+1}$ |
| ... | ... | ... | ... |
| $x_{\_k+a}$ | $x_{\_m+b}$ | $x_{\_n+c}$ | $x_{\_p+d}$ |

Referring to Table 1, gait feature vectors $x_{\_k}$ to $x_{\_k+a}$ of the user during the update period T belong to the walking speed range of 0 to 1 km/h, gait feature vectors $x_{\_m}$ to $x_{\_m+b}$ of the user during the update period T belong to the walking speed range of 1 to 2 km/h, gait feature vectors $x_{\_n}$ to $x_{\_n+c}$ of the user during the update period T belong to the walking speed range of 2 to 3 km/h, and gait feature vectors $x_{\_p}$ to $x_{\_p+d}$ of the user during the update period T belong to the walking speed range of 3 to 4 km/h.

The walking speed ranges of Table 1 are provided as examples only and the walking speed ranges disclosed herein are not limited thereto.

In one example embodiment, the information processing apparatus 110 may derive an average vector of gait feature vectors that belong to each walking speed range and may determine the average vector of each walking speed range as a gait vector of the user in each corresponding walking speed range. For example, when the average vector of the gait feature vectors $x_{\_k}$ to $x_{\_k+a}$ is $x_{1\_1}$, the information processing apparatus 110 may determine the average vector $x_{1\_1}$ as the gait feature of the user in the walking speed range of 0 to 1 km/h during the update period P. When the average vector of the gait feature vectors $x_{\_m}$ to $x_{\_m+b}$ is $x_{2\_1}$, the information processing apparatus 110 may determine the average vector $x_{2\_1}$ as the gait feature of the user in the walking speed range 1 to 2 km/h during the update period T. Also, when the average vector of the gait feature vectors $x_{\_n}$ to $x_{\_n+c}$ is $x_{3\_1}$, the information processing apparatus 110 may determine the average vector $x_{3\_1}$ as the gait feature of the user in the walking speed range 2 to 3 km/h during the update period T. When the average vector of the gait feature vectors $x_{\_p}$ to $x_{\_p+d}$ is $x_{4\_1}$, the information processing apparatus 110 may determine the average vector $x_{4\_1}$ as the gait feature of the user in the walking speed range 3 to 4 km/h during the update period T.

The description made above with reference to FIGS. 4 and 5 may apply to an example in which the information processing apparatus 110 determines the gait feature of the user of each of the other walking assistance apparatuses 120-2 to 120-n and thus, a further description related thereto is omitted.

An example of a result of determining, by the information processing apparatus 110, the gait feature of the user of each of the walking assistance apparatuses 120-1 to 120-n for each walking speed range during the update period T is shown in the following Table 2.

TABLE 2

| 0 to 1 km/h | 1 to 2 km/h | 2 to 3 km/h | 3 to 4 km/h |
|---|---|---|---|
| $x_{1\_1}$ | $x_{2\_1}$ | $x_{3\_1}$ | $x_{4\_1}$ |
| $x_{1\_2}$ | $x_{2\_2}$ | $x_{3\_2}$ | $x_{4\_2}$ |
| ... | ... | ... | ... |
| $x_{1\_n}$ | $x_{2\_n}$ | $x_{3\_n}$ | $x_{4\_n}$ |

Referring to Table 2, $x_{1\_1}$ denotes, for example, a gait feature of the user of the walking assistance apparatus 120-1 during the update period T, $x_{1\_2}$ denotes, for example, a gait feature of the user of the walking assistance apparatus 120-2 during the update period T, and $x_{1\_n}$ denotes a gait feature of the user of the walking assistance apparatus 120-n during the update period T.

In a subsequent update period, the information processing apparatus 110 may determine a gait feature of the user of each of the walking assistance apparatuses 120-1 to 120-n. The description made above with reference to FIGS. 4 and 5 may also be applied. Accordingly, a further description is omitted here.

Figure 6:
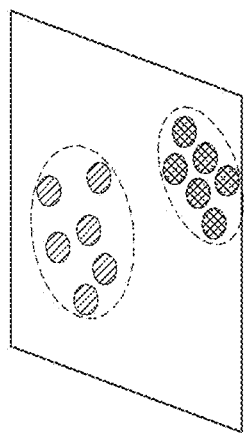
FIGS. 6 and 7 illustrate examples of determining, by an information processing apparatus, a gait group according to at least one example embodiment.
Figure 6:
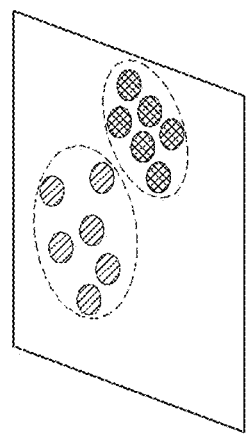
Figure 6:
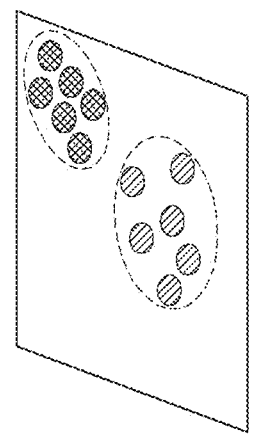
Figure 6:
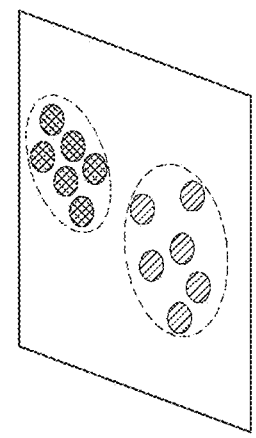
Figure 7:
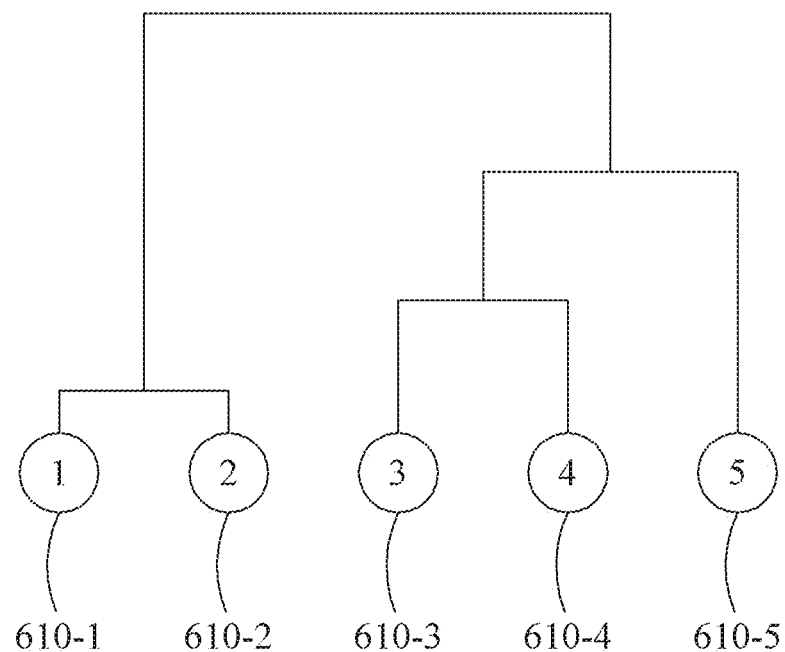

FIGS. 6 and 7 illustrate examples of determining, by an information processing apparatus, a gait group according to at least one example embodiment.

Referring to FIG. 6, the information processing apparatus 110 may perform clustering, for example, hierarchical clustering based on gait feature vectors that belong to each walking speed range. In the example of FIG. 6, the information processing apparatus 110 may perform clustering based on the gait feature vectors $x_{1\_1}$ to $x_{1\_n}$ that are classified into the walking speed range 0 to 1 km/h of Table 2. For example, the information processing apparatus 110 may calculate a distance of each of the gait feature vectors $x_{1\_1}$ to $x_{1\_n}$ according to the following Equation 3, and may form clusters based on the distance of each of the gait feature vectors $x_{1\_1}$ to $x_{1\_n}$.

$$L = x^T W x \quad \text{[Equation 3]}$$

In Equation 3, L denotes a distance and W denotes a weight vector.

Likewise, the information processing apparatus 110 may perform clustering based on the gait feature vectors $x_{2\_1}$ to $x_{2\_n}$ that are classified into the walking speed range 1 to 2 km/h of Table 2, may perform clustering based on the gait feature vectors $x_{3\_1}$ to $x_{3\_n}$ that are classified into the walking speed range 2 to 3 km/h of Table 2, and may perform clustering based on the gait feature vectors $x_{4\_1}$ to $x_{4\_n}$ that are classified into the walking speed range 3 to 4 km/h of Table 2.

FIG. 7 illustrates a clustering result in the walking speed range 0 to 1 km/h.

Referring to FIG. 7, a total of five clusters 610-1 to 610-5 may be generated. A number of the clusters 610-1, 610-2, 610-3, 610-4, and 610-5 is provided as an example only. Although it is not illustrated in FIG. 7, a plurality of clusters may be generated in each of the walking speed range of 1 to 2 km/h, the walking speed range of 2 to 3 km/h, and the walking speed range of 3 to 4 km/h.

In the example of FIG. 7, the gait feature vector $x_{1\_1}$ of the user of the walking assistance apparatus 120-1 may belong to the cluster 610-2, the gait feature vector $x_{1\_2}$ of the user of the walking assistance apparatus 120-2 may belong to the cluster 610-1, and the gait feature vector $x_{1\_n}$ of the user of the walking assistance apparatus 120-n may belong to the cluster 610-4.

The information processing apparatus 110 may transmit walking strategy information of a determined gait group of a corresponding user to a walking assistance apparatus of the corresponding user. For example, when the cluster 610-1 corresponds to a group of stroke patients with hemiplegia, the information processing apparatus 110 may transmit walking strategy information within the walking speed range of 0 to 1 km/h to the walking assistance apparatus 120-2. Here, the walking strategy information may include, for example, a torque profile to apply an assistance force using an asymmetric assistance method.

In one example embodiment, the information processing apparatus 110 may monitor recovery or deterioration of degree of pathological walking of the user and may modify the walking strategy information of the user based on a monitoring result. For example, when the pathological walking of the user belonging to the cluster 610-1 is deteriorated, the information processing apparatus 100 may transmit, to the walking assistance apparatus of the user, the walking strategy information in which the before-deterioration torque profile is modified.

Figure 8:
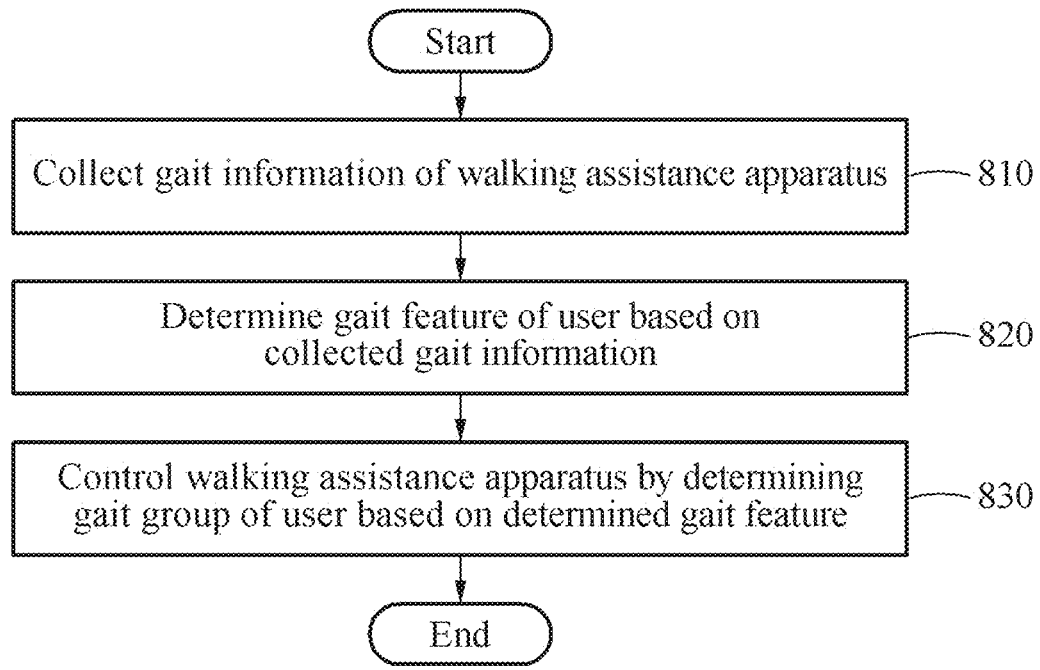
FIG. 8 is a flowchart illustrating an example of a method of operating an information processing apparatus according to at least one example embodiment.

FIG. 8 is a flowchart illustrating an example of a method of operating an information processing apparatus according to at least one example embodiment.

Referring to FIG. 8, in operation 810, the information processing apparatus 110 collects gait information of the walking assistance apparatus 120-1.

In operation 820, the information processing apparatus 110 determines a gait feature of the user of the walking assistance apparatus 120-1 based on the collected gait information.

In operation 830, the information processing apparatus 110 controls the walking assistance apparatus 120-1 by determining a gait group of the user based on the determined gait feature.

The descriptions made above with reference to FIGS. 1 to 7 may apply to FIG. 8 and thus, a further description is omitted here.

Figure 9:
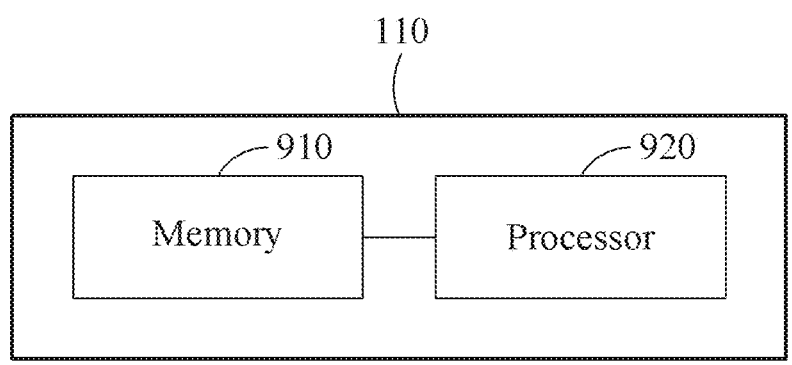
FIG. 9 illustrates an example of an information processing apparatus according to at least one example embodiment.

FIG. 9 illustrates an example of an information processing apparatus according to at least one example embodiment.

Referring to FIG. 9, the information processing apparatus 110 includes a memory 910 and a processor 920. Further, the information processing apparatus 110 may further include a communication interface. For example, the communication interface may include a wired or wireless communication device capable of transmitting and/or receiving information with the walking assistance apparatuses 120-1 to 120-n over, for example, a network, in a wired or wireless environment.

The memory 910 stores gait information of the walking assistance apparatus 120-1. The memory 910 stores gait information of each of the other walking assistance apparatuses 120-2 to 120-n.

Further, the memory 910 may store instructions that, when executed by processing circuitry included in, for example, the processor 920, configures the processor 920 as a special purpose computer to determine a gait feature of the user of the walking assistance apparatus 120-1 based on the gait information of the walking assistance apparatus 120-1 and controls the walking assistance apparatus 120-1 by determining a gait group of the user based on the determined gait feature. Therefore, the processing circuitry may improve the functioning of the walking assistance apparatus 120-1 by performing qualitative evaluation of a gait of the user from a remote location and provide feedback to accurately control the walking assistance apparatus 120-1 based on the evaluation.

Likewise, the processor 920 determines a gait feature of a user of each of the other walking assistance apparatuses 120-2 to 120-n based on gait information of each of the other walking assistance apparatuses 120-2 to 120-n and controls each of the other walking assistance apparatuses 120-2 to 120-n by determining a gait group of each user based on the determined gait feature of each user.

The descriptions made above with reference to FIGS. 1 to 8 may apply to FIG. 9 and thus, a further description is omitted here.

Figure 10:
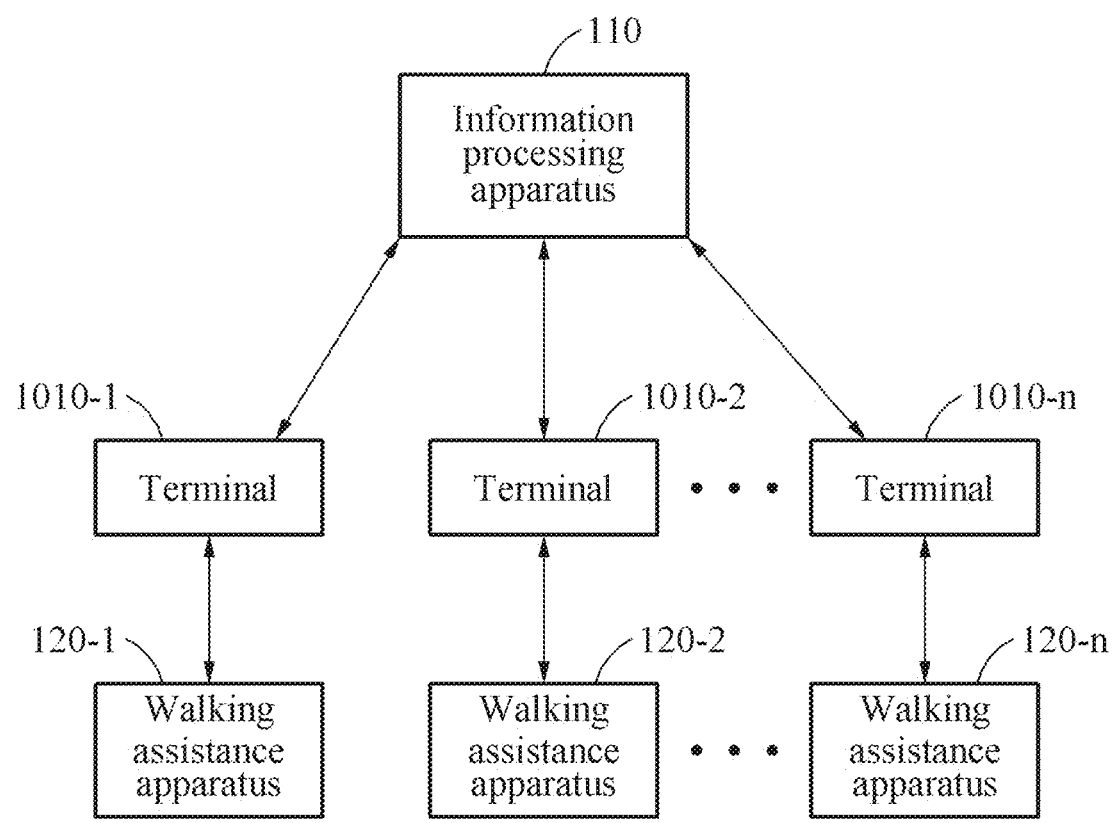
FIG. 10 illustrates another example of a walking system according to at least one example embodiment.

FIG. 10 illustrates another example of a walking system according to at least one example embodiment.

Referring to FIG. 10, a walking system 1000 includes an information processing apparatus 110, a plurality of walking assistance apparatuses 120-1 to 120-n, and a plurality of terminals 1010-1 to 1010-n.

Each of the plurality of terminals 1010-1 to 1010-n may be a mobile terminal, for example, a smartphone and a tablet, or a fixed terminal, for example, a personal computer (PC).

The plurality of walking assistance apparatuses 120-1 to 120-n and the plurality of terminals 1010-1 to 1010-n may be connected to each other, respectively, in a wired or wireless manner. For example, the plurality of walking assistance apparatuses 120-1 to 120-n and the plurality of terminals 1010-1 to 1010-n may form a near field wireless network, for example, Bluetooth and ZigBee, respectively.

Each of the plurality of walking assistance apparatuses 120-1 to 120-n may transmit gait information to the information processing apparatus 110 through each corresponding terminal among the plurality of terminals 1010-1 to 1010-n. Also, each of the plurality of walking assistance apparatuses 120-1 to 120-n may receive walking strategy information from the information processing apparatus 110 through each corresponding terminal among the plurality of terminals 1010-1 to 1010-n.

The descriptions made above with reference to FIGS. 1 to 9 may apply to FIG. 10 and thus, a further description is omitted here.

The units and/or modules described herein may be implemented using hardware components, software components, and/or combinations thereof. For example, the hardware components may include microphones, amplifiers, bandpass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

Example embodiments of the inventive concepts having thus been described, it will be obvious that the same may be varied in many ways. Such variations are not to be regarded as a departure from the intended spirit and scope of example embodiments of the inventive concepts, and all such modifications as would be obvious to one skilled in the art are intended to be included within the scope of the following claims.

What is claimed is:

1. A method of operating an information processing apparatus including a processor, the information processing apparatus being remotely connected to a plurality of walking assistance apparatuses via a communications interface, the method comprising:

receiving, from a walking assistance apparatus among the plurality of walking assistance apparatuses, gait information of a user collected using at least one sensor of the walking assistance apparatus and transmitted to the information processing apparatus via the communications interface;

determining gait indices of the user based on the gait information, the gait indices including at least a walking speed of the user;

generating a first gait feature vector of the user based on the gait indices;

obtaining second gait feature vectors of other users, the second gait feature vectors being clustered into a plurality of gait groups each assigned to a different walking speed range, each of the plurality of gait groups having a torque profile associated therewith;

determining a selected gait group from among the plurality of gait groups having a walking speed range that overlaps the walking speed of the user;

clustering on the first gait feature vector of the user into the selected gait group;

and transmitting, to the walking assistance apparatus, the torque profile associated with the selected gait group such that the walking assistance apparatus provides a torque to the user based on the torque profile associated with the selected gait group.

2. The method of claim 1, wherein the gait indices further include at least one of a number of steps of the user, a step length of the user, a gait symmetry of the user, a motion range of the user in a roll direction of walking, and a motion range of the user in a pitch direction of walking.

3. The method of claim 2, wherein the gait symmetry indicates a level of symmetry between legs of the user while the user is walking.

4. The method of claim 1, further comprises:
applying a weight vector to the first gait feature vector.

5. The method of claim 1, wherein the determining the gait indices comprises:

determining the walking speed of the user based on at least one of acceleration information and angular velocity information associated with the walking assistance apparatus;

and determining a gait symmetry of the user based on a first ratio and a second ratio, the first ratio being a time of a swing phase over a time of a stance phase of a left foot of the user, and the second ratio being a time of a swing phase over a time of a stance phase of a right foot of the user.

6. The method of claim 1, wherein the determining the gait indices comprises:

determining a number of steps of the user based on a swing count of an encoder associated with the walking assistance apparatus;

and determining a step length of the user based on at least one of a motion range, an angular velocity range, and an angular acceleration range of hip joints of the user.

7. The method of claim 1, wherein the determining the gait indices comprises:

determining an angle of a motion in each of a roll direction and a pitch direction based on measurements obtained by an inertial sensor associated with the walking assistance apparatus.

8. The method of claim 1, wherein the gait information includes at least one of (i) acceleration information and angular velocity information associated with the walking assistance apparatus and (ii) angle information and the angular velocity information associated with the walking assistance apparatus.

9. An information processing apparatus comprising:

a communication interface connected to a plurality of walking assistance apparatuses such that the information processing apparatus is remotely connected to the plurality of walking assistance apparatuses via the communications interface;

a memory configured to store gait information for a user collected using at least one sensor of a walking assistance apparatus among the plurality of walking assistance apparatuses and transmitted to the information processing apparatus via the communications interface;

and a processor configured to:

determine gait indices of the user based on the gait information, the gait indices including at least a walking speed of the user, generate a first gait feature vector of the user based on the gait indices;

obtain second gait feature vectors of other users, the second gait feature vectors being clustered into a plurality of gait groups each assigned to a different walking speed range, each of the plurality of gait groups having a torque profile associated therewith;

determine a selected gait group from among the plurality of gait groups having a walking speed range that overlaps the walking speed of the user;

cluster the first gait feature vector of the user into the selected gait group;

and transmit, to the walking assistance apparatus, the torque profile associated with the selected gait group such that the walking assistance apparatus provides a torque to the user based on the torque profile associated with the selected gait group.

10. The information processing apparatus of claim 9, wherein the gait indices further include a number of steps of the user, a step length of the user, a gait symmetry of the user, and a motion range of the user in a roll direction of walking, and a motion range of the user in a pitch direction of walking.

11. The information processing apparatus of claim 10, wherein the gait symmetry indicates a level of symmetry between legs of the user while the user is walking.

12. The information processing apparatus of claim 9, wherein the processor is further configured to apply a weight vector to the first gait feature vector.

13. The information processing apparatus of claim 9, wherein the processor is further configured to, determine the walking speed of the user based on at least one of acceleration information and angular velocity information of the walking assistance apparatus, and determine a gait symmetry of the user based on a first ratio and a second ratio, the first ratio being a time of a swing phase over a time of a stance phase of a left foot of the user and the second ratio being a time of a swing phase over a time of a stance phase of a right foot of the user.

14. The information processing apparatus of claim 9, wherein the processor is further configured to, determine a number of steps of the user based on a swing count of an encoder associated with the walking assistance apparatus, and determine a step length of the user based on at least one of a motion range, an angular velocity range, and an angular acceleration range of hip joints of the user.

15. The information processing apparatus of claim 9, wherein the processor is further configured to determine an angle of a motion in each of a roll direction and a pitch direction based on measurements obtained by an inertial sensor associated with the walking assistance apparatus.

16. The information processing apparatus of claim 9, wherein the gait information includes at least one of (i) acceleration information and angular velocity information associated with the walking assistance apparatus, and (ii) angle information and the angular velocity information associated with the walking assistance apparatus.

\* \* \* \* \*